United States Patent [19]
Takeda et al.

[11] Patent Number: 5,244,798
[45] Date of Patent: Sep. 14, 1993

[54] REAGENT FOR DETERMINING TRIGLYCERIDES COMPRISING A THERMOSTABLE LIPOPROTEIN LIPASE FROM STREPTOMYCES

[75] Inventors: Akira Takeda; Tomoko Kamei; Masao Kageyama; Kenzo Motosugi, all of Kyoto, Japan

[73] Assignee: Unitika Ltd., Hyogyo, Japan

[21] Appl. No.: 929,743

[22] Filed: Aug. 17, 1992

Related U.S. Application Data

[62] Division of Ser. No. 391,017, Aug. 9, 1989, Pat. No. 5,173,417.

[30] Foreign Application Priority Data

Aug. 9, 1988 [JP] Japan ................................. 63-199639

[51] Int. Cl.$^5$ ................ C12N 9/20; C12N 9/00; C12Q 1/44; G01N 33/00
[52] U.S. Cl. .................................. 435/198; 435/186; 435/253.5; 435/906; 436/86
[58] Field of Search .................. 435/198, 186, 253.5, 435/906; 436/86

[56] References Cited

U.S. PATENT DOCUMENTS 4,283,494 8/1981 Kokusko et al. ................. 435/198

FOREIGN PATENT DOCUMENTS 1117474 6/1968 United Kingdom .

OTHER PUBLICATIONS

Mamarw et al. (1968) *Gifu Yakka Daigakw Kiyo*, 18, 47–53, in *Chem Abst.*, 72 (1970), 34, Abst #62942.
Tadahiko (1977) *Jpn. Kokai Tokkyo Koho*, 7,8,104,792, in *Chem Abst.*, 90 (1979) 436, Abst. #101,958.
Okawa et al. (1975) *J. Biochem*, 78, 363–372.
Okawa et al. (1975) *J. Biochem.*, 78, 537–545.
Yamaguchi et al. (1973) *Agri. Biol. Chem.*, 37(7), 1667–1672.
Aisaka et al. (1980) *Agric. Biol. Chem*, 44, 799–805.

*Primary Examiner*—Douglas W. Robinson
*Assistant Examiner*—Jon P. Weber
*Attorney, Agent, or Firm*—Sughrue, Mion, Zinn, Macpeak & Seas

[57] ABSTRACT

A reagent composition for determining blood triglycerides comprising a color former and a thermostable lipoprotein lipase obtained from Streptomyces 7825 (FERM P-9983, FERM BP-2489) is presented.

3 Claims, 2 Drawing Sheets

OPTIMUM pH pH STABILITY

OPTIMUM TEMPERATURE

HEAT STABILITY

REAGENT FOR DETERMINING TRIGLYCERIDES COMPRISING A THERMOSTABLE LIPOPROTEIN LIPASE FROM STREPTOMYCES

This is a divisional of application Ser. No. 07/391,017 filed Aug. 9, 1989 now U.S. Pat. No. 5,173,417.

FIELD OF THE INVENTION

This invention relates to a lipoprotein lipase having excellent thermostability and high glycerol formation activity, a process for preparing the same, and a reagent containing the same which is useful for quantitative determination of triglycerides.

BACKGROUND OF THE INVENTION

The existence of lipoprotein lipase (hereinafter referred to an "LPL") as a clearing factor was recognized in 1943 by P. F. Hahn through his study on the circulatory amount of red blood cells. P. F. Hahn found that the injection of heparin to an alimentary lipemic dog results in clearing of the milky plasma. Thereafter, it was elucidated that the clearing mechanism is due to the hydrolysis of lipoprotein with LPL. LPL had been detected in the tissues of various animals. Thus, LPL plays an important role in lipid metabolism in animals.

Arima et al, *Agr. Biol. Chem.*, Vol. 30, p. 515 (1966) reported that an enzyme similar to LPL of animal origin exists in microorganisms and this enzyme has been called microbial LPL. Because the microbial LPL can be produced in large quantity, studies on the utilization of microbial LPL have been promoted. In particular, applications regarding the quantitative determination of triglycerides in blood have been developed.

Microorganisms capable of producing LPL include various genera such as Pseudomonas, Mucor, Streptomyces, Serratia, Aeromonnas, Bacillus (see *Agr. Biol Chem.*, Vol. 31, p. 924 (1967), JP-B-41-7836, and JP-B-58-37835 (the term "JP-B" as used herein means an "examined published Japanese patent application"), and Rhizopus (see *Agr. Biol. Chem*, Vol. 43, p. 2125 (1979), and JP-B-58-37834). However, since all of these microorganis are mesophiles, LPL produced therefrom exhibits poor stability.

With the recently increasing use of enzyme assays in clinical examinations, the unstability of enzymes has given rise to great problems. Techniques for obtaining thermostable enzymes from thermophilic microorganisms, have been developed to improve enzyme stability.

However, thermostable LPL has not yet been developed and has thus been keenly demanded.

Further, in cases when LPL is used in the quantitative determination of triglycerides in blood, LPL must exhibit high activity to form glycerol so as to reduce the requisite amount of the reagent used and to shorten the reaction time required. Thus, the use of any known LPL is not satisfactory.

It is known that lipases inclusive of LPL exhibit specificity to the three ester linkages of a triglyceride substrate. In the quantitative determination of blood triglyceride using LPL, glycerol formed by hydrolysis is preferably introduced into a detection system by a coupling enzyme. In order to form glycerol in an amount proportional to the triglyceride amount, it is preferable to use an LPL capable of hydrolyzing the three ester linkages without showing selectivity. The positional specificity of known LPL to ester linkages, being expressed in a percentage of glycerol formation activity to fatty acid formation activity, is generally low. The highest of the cases reported so far, is 1.97% of LPL originating in a microorganism belonging to the genus Pseudomonas as described in JP-A-59-187780 (the term "JP-A" as used herein means an "unexamined published Japanese patent application").

SUMMARY OF THE INVENTION

One object of this invention is to provide an LPL having excellent thermostability and high glycerol formation activity.

Another object of this invention is to provide a process for producing such an LPL.

A further object of this invention is to provide a triglyceride determining reagent containing such an LPL.

The inventors have searched extensively for microorganisms capable of producing the above-described LPL. As a result, it has now been found that a thermophilic actinobacterium (Streptomyces 7825 (FERM P-9983, FERM BP-2489) isolated from the soil of Izu Atagawa, Shizuoka, Japan is capable of producing LPL having the above-described properties.

That is, the present invention relates to a thermostable LPL able to hydrolyze triglycerides in lipoprotein to glycerol and fatty acids. The LPL, after treatment in a buffer having a pH of from about 4 to 7 at a temperature of about 60° C. for about 15 minutes, retains about 100% of its hydrolyzing activity, and the glycerol forming activity of which is at least about 15% of the fatty acid forming activity.

The present invention further relates to a process for producing thermostable LPL which comprises cultivating a thermophilic actinomycetes and recovering thermostable LPL from the culture.

The present invention furthermore relates to a reagent containing LPL for the quantitative determination of triglycerides in body fluids, wherein said LPL has an activity to hydrolyze triglycerides in lipoproteins to glycerol and fatty acids, said hydrolyzing activity being about 100% retained after treatment in a buffer at a temperature of about 60° C. for about 15 minutes, and the ratio of glycerol forming activity to fatty acid forming activity being at least about 15%.

The LPL according to the present invention is superior to conventionally known LPL's in thermostability and in the ratio of glycerol formation activity to fatty acid formation activity. Therefore, when used as a test reagent, the LPL makes it possible to considerably extend the life time of the reagent while reducing a time required for determination per sample, thus greatly contributing to the industry.

DETAILED DESCRIPTION OF THE INVENTION

The hydrolysing activity of the present LPL is retained at a retention of about 100% when it is treated in a buffer at about 60° C. for about 15 minutes. The concentration and pH of the buffer herein referred to are not particularly limited but, usually, the concentration ranges from about 5 to 500 mM, preferably about 10 to 250 mM, more preferably about 20 to 100 mM, and the pH ranges from about 4 to 7, preferably about 4.5 to 6, more preferably about 5. It is particularly preferable to use an acetic acid buffer (pH=5.0).

The LPL of the present invention produced by Streptomyces 7825 (FERM P-9983, FERM BP-2489) has the following physiochemical properties:

(a) Action

It acts on triglycerides of lipoproteins to hydrolyze them into glycerol and fatty acids. The lipoproteins include not only artificial lipoproteins but human blood lipoproteins.

(b) Substrate Specificity

It exhibits activity on lipoproteins consisted of various triglycerides as shown in Table 1 below. In Table 1, the activity is expressed relative to an olive oil as a standard (100%).

TABLE 1

Figure 1:
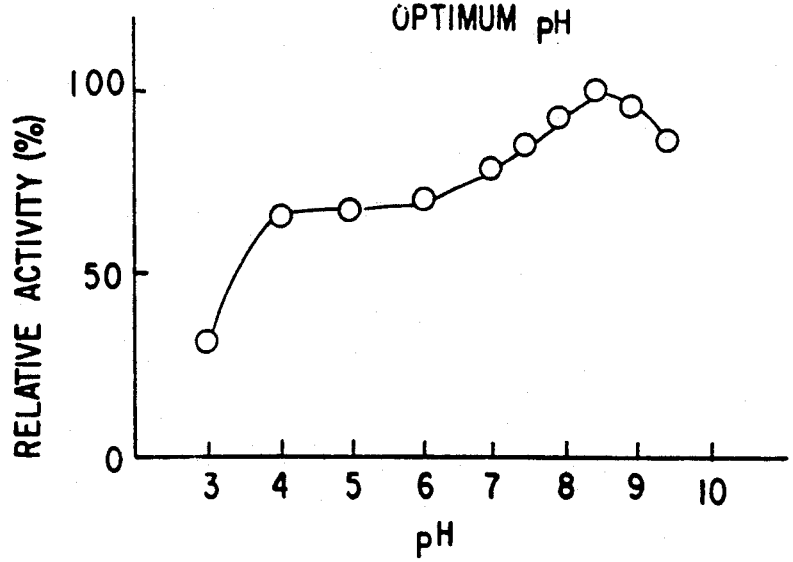
FIG. 1 is a graph showing the optimum pH of the LPL of the present invention.
Figure 2:
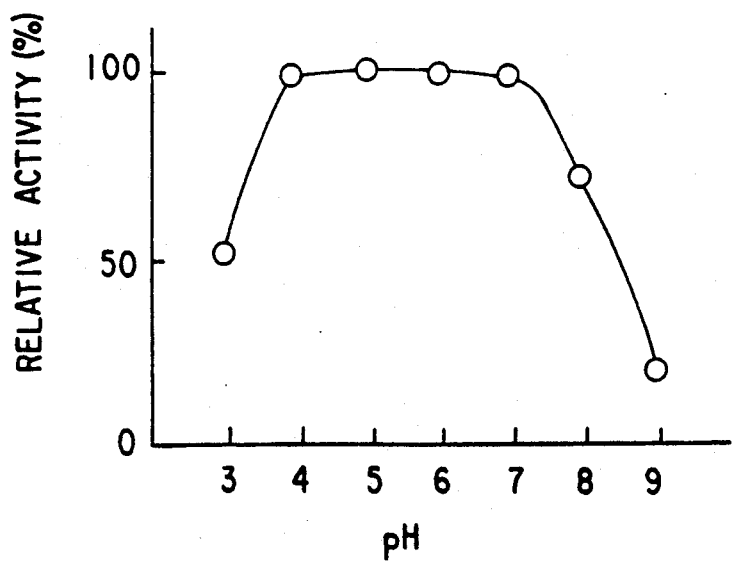
FIG. 2 is a graph showing pH stability of the LPL of the present invention.
Figure 3:
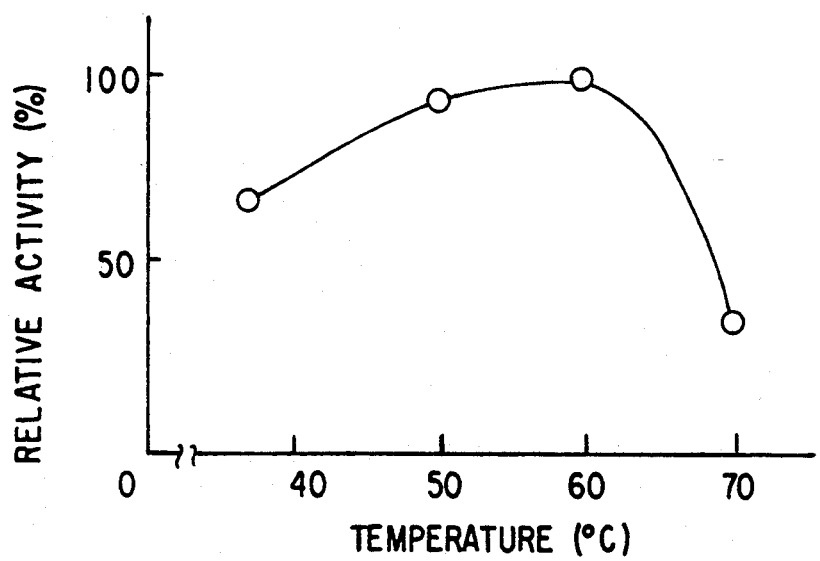
FIG. 3 is a graph showing the optimum temperature of the LPL of the present invention.

| Substrate Specificity | |
|---|---|
| Triglyceride | Relative Activity (%) |
| Triacetin | 28 |
| Tributyrin | 22 |
| Tricaproin | 46 |
| Tricaprylin | 148 |
| Tricaprin | 153 |
| Trilaurin | 234 |
| Tripalmitin | 99 |
| Tristearin | 29 |
| Triolein | 75 |
| Olive Oil | 100 |
| (c) Optimum pH: | 8.0 to 9.0 as shown in FIG. 1 |
| Stable pH: | 4.0 to 7.0 (when treated at 60°, 30 mins.) as shown in FIG. 2. |
| (d) Optimum Acting Temperature: | 50 to 60° C. as shown in FIG. 3. |

(e) Heat Stability

Figure 4:
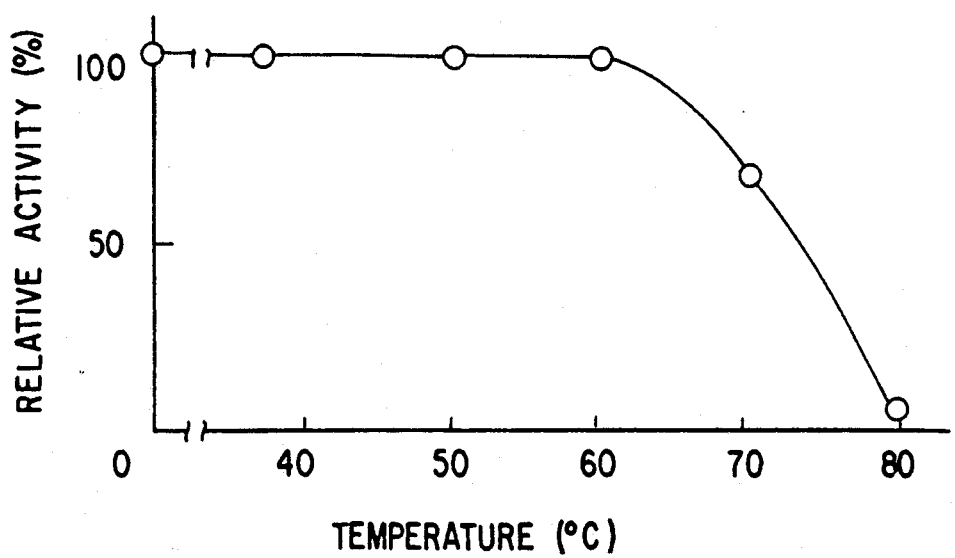
FIG. 4 is a graph showing heat stability of the LPL of the present invention.

About 100% of the activity can be retained after treatment in 50 mm acetate buffer (pH 5.0) at about 60° C. for about 15 minutes as shown in FIG. 4.

(f) Inhibition

It is 30 to 40% inhibited by $Zn^{2+}$, $Fe^{3+}$, and $Mg^{2+}$ each at a concentration of 1 mM, about 40% inhibited by 3M NaCl, about 40% inhibited by 10 mM deoxycholic acid, or about 30% inhibited by 400 μg/ml protamine sulfate.

(g) Molecular Weight: 30,000 to 50,000 (gel-filtration)

(h) Titer

Titer determination is principally based on the quantitative determination of glycerol formed through the action of LPL on artificial lipoprotein prepared from olive oil as described in *Clin. Chim. Acta.*, Vol. 22, p. 393 (1968).

REAGENT

A mixture of 5 g of olive oil and 5 ml of a 5% (v/v) Triton X-100 solution is subjected to ultrasonication for 10 minutes to prepare a substrate emulsion.

12 ml of 25 mM metaperiodic acid and 20 ml of isopropanol are mixed. 1N acetic acid is added thereto to make 100 ml.

2,4-Pentanedione (0.75 ml) and 2.5 ml of isopropanol are mixed, and 2M ammonium acetate is added thereto to make 100 ml.

PROCEDURE

Seventy microliters of the abovementioned substrate solution, 20 μl of a 0.5M glycine buffer (pH 8.5), 50 μl of 10% (w/v) BSA, and 55 μl of water are mixed in a test tube, and the system is preheated at 37° C. 5 μl of an enzyme solution having an enzyme concentration adjusted to about 10 U/ml, is added to the system. The system is then allowed to react at 37° C. for 10 minutes. After completion of the reaction, the test tube is soaked in boiling water to stop the reaction. After allowing the test tube to cool, 400 μl of isopropanol is added to the reaction system, followed by stirring. The mixture is then centrifuged. 2 ml of isopropanol is then added to 100 μl of the supernatant liquor. The solution is mixed with 1 ml of the above prepared metaperiodic acid solution and 0.5 ml of the above prepared acetylacetone solution to effect a reaction at 50° C. for 30 minutes. The absorbance of the system at 405 nm is measured. A blank estimation (control) is run on a system containing no enzyme solution.

From the measured values, a calibration curve is prepared using a glycerol solution having a known concentration. Thus the glycerol content of the reaction mixture is determined using the prepared calibration curve.

The enzyme activity is expressed by taking the amount of the enzyme which forms 1 μmol of glycerol per minute as 1U.

(i) Ratio of Glycerol Formation Activity

The glycerol formation activity of the LPL is at least about 15% of the fatty acid formation activity. While activity is generally expressed in terms of glycerol formation activity as stated above, it is necessary to obtain the fatty acid formation activity before the ratio of glycerol formation activity to fatty acid formation activity can be obtained. The fatty acid formation activity can be determined by assaying an isopropanol extract obtained in the same manner as described above for the formed fatty acid content by the use of a commercially available kit for determining free fatty acids (e.g., NEFAC-Test produced by Wako Pure Chemical Industries, Ltd.), taking the amount of the enzyme capable of forming 1μ equivalent of fatty acids per minute as 1U.

Accordingly, the ratio of glycerol formation activity to fatty acid formation activity can be calculated from formula:

Glycerol Formation Activity (U)/Fatty Acid Formation Activity (U)×100

(j) Purification Method: As hereinafter described.

(k) Crystal Structure and Elementary Analysis: Unconfirmed.

The LPL according to the present invention can be produced by cultivating a thermophilic actinomycetes and recovering the produced and accumulated LPL from the culture.

The thermophilic actinomycetes for use in the present invention is not limited as long as it is capable of producing the LPL of the invention. One example of such a microorganism is Streptomyces 7825 isolated from the soil. The microbiological properties of this strain are described below.

The experiments for the determination of the microbiological properties were in accordance with the methods described in Nippon Hosenkin Kenkyukai (ed.),

*Hosenkin no Dotei Jikkenho* (Identification Test Method of Actinomycetes), (1975) and Kazuo Komagata (ed.), *Biseibutsu no Kagaku Bunrui Jikkenho* (Chemical Classification Test Method of Microorganisms) (1982).

(a) Morphology

The culture after cultivation by slide cell culture in a nutrient agar medium at 50° C. for 4 days was observed under a microscope and a scanning electron microscope.

Branching of sporulating hypha: simple branching.
Form of sporulating hypha: curved and spiral.
Number of spores: 10 or more.
Surface structure and size of spore: smooth, 0.5 to 1.0 $\mu m \times 1.0$ to 1.5 $\mu m$ in diameter.
Flagellospore: none.
Sporangium: none.
Growth position of sporephore: on aerial hyphae.
Sclerotium formation: none.

(b) Growth State in Various Media (on culturing at 50° C. for 6 days)

(1) Sucrose-nitrate-agar medium:
Spreading and flat milky colonies with thin powderous brown aerial hyphae.

(2) Glucose-asparagine-agar medium:
Spreading and flat milky colonies with no aerial hyphae.

(3) Glycerin-asparagine-agar medium:
Spreading and flat milky colonies with no aerial hyphae.

(4) Starch-agar medium:
Spreading and flat milky colonies with abundant powderous brown aerial hyphae.

(5) Tyrosine-agar medium:
Spreading and swollen milky colonies with thin powderous white aerial hyphae, brown pigment formed in the surrounding agar.

(6) Nutrient agar medium:
Spreading and swollen milky colonies with abundant powderous gray aerial hyphae.

(7) Yeast-malt-agar medium:
Spreading and wrinkled milky colonies with abundant powderous gray aerial hyphae.

(8) Oatmeal-agar medium:
Spreading and flat milky colonies with no aerial hyphae.

(c) Physiological Properties (1) Growth temperature range: 2° to 55° C.
(2) Liquefaction of gelatin: +.
(3) Hydrolysis of starch: +.
(4) Coagulation and peptonization of skim milk: −.
(5) Formation of melanin-like pigment: +.

(d) Carbon Source Assimilability (1) L-Arabinose: ±.
(2) D-Xylose: + +.
(3) D-Glucose: + +.
(4) D-Fructose: + +.
(5) Sucrose: ∓.
(6) Inositol: + +.
(7) L-Rhamnose: ∓.
(8) Raffinose: ∓.
(9) D-Mannitol: + +.

+ +: Strongly assimilative. Equal to or higher than glucose assimilability.

±: Doubtful. Slightly higher than control but much lower than glucose assimilability.

∓: Non-assimilative. Equal to control and greatly lower than glucose assimilability.

(e) Chemical Composition of Cell Wall: cell wall type I

As a result of studying the above-described microbiological properties in accordance with *Bergey's Manual of Determinative Bacteriology*, 8th Ed., this strain was identified to belong to the genus Streptomyces. As a result of further research, the strain was found nearly consistent with Streptomyces galbus in terms of spore color, form of sporephore, surface structure of spore, production of melanin-like pigment, and carbon source assimilability, except for differences in L-arabinose assimilability and color of the hyphae. Thus, the strain was judged to be similar to but not the same as *Streptomyces galbus*. The strain was designated as Streptomyces 7825 and deposited in the Agency of Fermentation Research Institute, Japan (FERM P-9983, FERM BP-2489).

This strain is capable of producing the present LPL by culturing in an appropriate liquid nutrient medium containing an inducer. After completion of the cultivation, the culture filtrate is collected and purified through various known methods as described, for example, in *Method in Enzymoloqy*, vol. 22, edited by W. B. Jakoby, Academic press (1971) to obtain the LPL of the present invention.

In more detail, since LPL synthesis by the strain is induced, the addition of an inducer to the medium is desirable. Suitable inducers include fats and oils and fatty acids. The fats and oils include animal oils, e.g., lard, butter, fish oil, and whale oil; and vegetable oils, e.g., olive oil, soybean oil, rice bran oil, cotton seed oil, and sesami oil. The fatty acids include oleic acid, palmitic acid, and linolenic acid. The amount of the inducer to be added is not particularly limited but preferably ranges from about 0.1 to 3% (w/v). The medium further comprises carbon sources, nitrogen sources and inorganic salts generally employed for the cultivation of actinomycetes. Suitable carbon sources include glucose, glycerol, and soluble starch. Suitable nitrogen sources include peptone, urea, ammonium sulfate, corn steep liquor, defatted soybean flour, yeast extract, and meat extract. Suitable inorganic salts include monopotassium hydrogenphosphate, disodium hydrogenphosphate, and magnesium sulfate. To accelerate the secretion of LPL into the medium, the addition of a surface active agent is effective. In particular, it is preferable to add about 0.05 to 0.5% (w/v) of a nonionic surface active agent, e.g., Tween 40, Tween 60, or Tween 80. The medium is adjusted to a pH range of from about 6.0 to 7.5 in the vicinity of neutrality. Aerobic conditions, such as stirring under aeration, produce satisfactory results. The cultivation temperature usually ranges from about 30° to about 50° C., and preferably around 50° C. to reduce culturing time. Culturing for from about 1 to 6 days, preferably from about 3 to 5 days under these conditions results in the accumulation of a considerable quantity of LPL in the medium.

After completion of the cultivation, the mycelium pellets are removed from the culture, for example, by centrifugation or filtration to collect a liquid. Purification of the enzyme can be conducted by known purification procedures, such as salting-out with ammonium sulfate or organic solvent precipitation with acetone, alcohols, etc. to obtain a crude enzyme. The crude product can further be purified to a higher degree by various known chromatographic techniques, such as ion exchange chromatography, gel-filtration chromatography, and hydrophobic chromatography. Since the LPL of the present invention is strongly hydrophobic, hydrophobic chromatography is preferably applied to obtain a highly purified enzyme.

Since the LPL according to the present invention is very heat stable, it can be preserved for an extended period of time as compared to conventionally available LPL preparations. Thus, use of the present LPL is greatly advantageous.

For example, it is well known that LPL is useful as a reagent for the enzymatic assay of blood triglycerides. The assay is based on the principle that triglycerides in blood are hydrolyzed with LPL and the formed glycerol is quantitatively determined by enzymatic assay. The quantitative determination of glycerol can be carried out by methods utilizing glycerol kinase, glycerol dehydrogenase, and glycerol oxidase. The method utilizing is glycerol kinase commonly employed. According to the method utilizing glycerol kinase, three kinds of enzymes; glycerol kinase glycerol-3-phosphate oxidase, and peroxidase, are employed. Each of these enzymes, not limited in maker or origin, is used in concentrations of from about 1.0 to 2.5 U/ml in a determining reagent. The buffer to be used is not particularly limited, but a weakly acidic buffer such as citrate, $\beta,\beta'$-dimethylglutarate, acetate, succinate, futarate, phosphate or MES buffer is, preferably used. A suitable range of pH and concentration of the buffer is from about 5 to 7 and from about 10 to 100 mM, respectively. The reagent further contains ATP $Na_2 \cdot 3H_2O$ and $MgCl_2 \cdot 6H_2O$ which are necessary for the glycerol kinase reaction, in an amount of from 20 to 30 mg and from 3 to 50 mg, respectively, per 200 ml of the reagent. The reagent furthermore contains 4-aminoantipyrine and a color former in the range of from about 1 to 20 mg and from about 5 to 100 mg, respectively, per 200 ml of the reagent. The color former can be selected arbitrarily from phenol derivatives, aniline derivatives and toluidine derivatives such as p-hydroxydiphenyl, hydroquinone, hydroquinone monomethylether, cathechol, resorcinol, pyrogallol, o-phenylenediamine, m-phenylenediamine, aniline, diethylaniline, p-aminobenzoic acid, reductone and dimethyltoluidine. In order to increase solubility of the color formed, a surface active agent, e.g., Triton X-100, Span 20, sodium cholate, sodium dodecyl sulfate or dimethylbenzyl-alkyl-ammonium chloride, is preferably added. These surface active agents may be used in a concentration of about 1 to 10% (w/v) and a amount of about 2 to 10 ml, preferably a concentration of about 2 to 6% (w/v) and an amount of about 3 to 6 ml, per 200 ml of the reagent.

To 1 ml of the thus prepared determining reagent are added several microliters, preferably about 1 to 30 $\mu$l, more preferably 2 to 20 $\mu$l, most preferably 5 to 15 $\mu$l, of non-diluted serum, and several microliters of the LPL (5 to 10 U/ml) according to the present invention are then added thereto. The system is incubated in a cuvette whereby the color former develops a color in proportion to the amount of triglycerides in the serum The color formation is determined in terms of absorbance to quantitatively determine the amount of triglyceride in the sample.

The present invention is now illustrated in greater detail by way of the following Examples, but it should be understood that the present invention is not deemed to be limited thereto.

EXAMPLE 1

A medium (100 ml) comprising 0.5% of peptone, 0.1% of $KH_2PO_4$, 0.1% of $Na_2HPO_4 \cdot 12H_2O$, 0.05% of $MgSO_4 \cdot 7H_2O$, 0.03% of yeast extract, 0.2% of olive oil, and 0.5% of Tween 40 (pH 7.0) were placed in a 500 ml-volume Erlenmeyer flask and autoclaved at 121° C. for 15 minutes.

Separately, Streptomyces 7825 (FERM P-9983, FERM BP-2489) was cultured in a test tube containing 5 ml of the medium having the same composition as described above.

The culture liquid was inoculated into the above prepared medium and cultivated by rotary shaking culture at 50° C. for 3 days to obtain a seed culture for jar fermentation. 2 l of the same medium was charged into a 3 l-volume jar fermenter and autoclaved at 121° C. for 15 minutes. 100 ml of the seed culture was then inoculated thereto, followed by culturing at −50° C. under aeration of 1 VVM and stirring at 400 rpm.

After three days, the culture liquid was assayed for enzyme activity and found to contain 0.2 U/ml of LPL. The culturing was ended at this point, and the mycelium pellets were removed by filtration to recover the culture filtrate.

The culture filtrate was passed through a column (4.4 cm in diameter; 10 cm in height) packed with phenyl Sepharose pre-equilibrated with 25 mM phosphate buffer (pH 7.0). After the column was thoroughly washed with the same buffer, the buffer was changed to 25 mM phosphate buffer containing 1% Triton X-100, then LPL was eluted out showing a sharp elution peak. The active fractions were collected, concentrated, and passed through a column (2.2 cm in diameter, 90 cm in height) packed with Sephadex G-75 pre-equilibrated with a buffer containing 0.1% Triton X-100. The protein peak and the activity peak were consistent with each other. SDS-polyacrylamide gel electrophoresis of the active fractions gave a single band.

The resulting enzyme sample had a specific activity of 1.2 U/mg.

The amount of protein was quantitatively determined by Wang-Smith method (*Anal. Biochem.*, Vol. 63, p. 414 (1975)).

Upon examination of the resulting purified enzyme, the aforesaid physiochemical characteristics were confirmed. In particular, it was proved that the present LPL is superior in thermostability to other commercially available LPL's of microorganism origin. More specifically, when LPL's of Pseudomonas origin (product of TOYOBO Ltd.) or LPL's of Alcaliqenes origin (product of Meito Sangyo Co., Ltd ) were treated at 60° C. for 15 minutes at the pH at which the respective LPL's were most stable, i.e., 7.0 or 8.0, respectively, the retention of activity was about 70% or about 0%, respectively. The LPL of the present invention thus obtained showed an activity retention of approximately 100% when similarly treated at a pH of 5.0. The LPL of the present invention is most stable at a pH of 5.0.

The ratio of glycerol formation activity to fatty acid formation activity of the LPL of the present invention was found to be 16%, which is far higher than 1.97% attained by the LPL of Pseudomonas origin (product of TOYOBO Ltd.).

EXAMPLE 2

Blood triglyceride was determined using the reagent prepared from the LPL prepared in Example 1. The determination was carried out by hydrolyzing blood triglycerides with the LPL and assaying the formed glycerol with a coupling enzyme system comprising glycerol kinase, glycerol-3-phosphate oxidase, and peroxidase.

| Glycerol Color Forming Solution: | |
| --- | --- |
| 5% Triton X-100 | 4 ml |
| N,N-Diethyl-m-toluidine | 40 μl |
| 4-Aminoantipyrine | 4 mg |
| ATP Na$_2$.3H$_2$O | 25 mg |
| MgCl$_2$.6H$_2$O | 40 mg |
| Glycerol kinase | 200 U |
| Glycerol-3-phosphate oxidase | 500 U |
| Peroxidase | 300 purpurogallin U |

The above-described glycerol color forming solution was dissolved in a 50 mM MES buffer (pH 6.5) to make 200 ml. 10 μl of serum was added to 1 ml of the resulting solution, followed by pre-incubation at 37° C. for 3 minutes. The absorbance at 545 nm was read. Then 5 μl of the LPL obtained in Example 1 (adjusted to a concentration of 5 to 10 U/ml) was added thereto, followed by incubation at 37° C. The absorbance at 545 nm was measured.

Ten minutes later, where the absorbance had reached a constant level, an increase of absorbance (ΔA545) was obtained, and the triglyceride content was calculated therefrom according to equation:

$$\text{Triglyceride Content (mg-triolein/dl)} = \frac{\Delta A545 \times 1.015 \times 885.45}{28.2 \times 0.5 \times 1 \times 0.01 \times 10}$$

wherein ΔA545 is an increase of absorbance at 545 nm: 28.2 is a molecular extinction coefficient of the dyestuff (l/mmol/cm); 0.5 is a factor derived from the fact that 1 molecule of H$_2$O$_2$ forms ½ molecule of the dyestuff; 1 is a light pass length (cm); and 885.45 is the molecular weight of triolein.

For reference, triglyceride determinations were run with the above-described reagent on two kinds of commercially available controlled serum preparations produced by Wako Pure Chemical Industries, Ltd., whose triglyceride contents were indicated to be 104 mg/dl and 280 mg/dl, respectively. As a result, the triglyceride content of these preparations were found to be 104 mg/dl and 280 mg/dl, respectively.

On the other hand, the triglyceride content of the same controlled serum preparations was determined by the method of saponification with potassium hydroxide as described in *Clin. Chim. Acta*, Vol. 22, p. 393 (1968). The measured values were 103 mg/dl and 279 mg/dl, respectively, being consistent with those obtained with the reagent containing the LPL according to the present invention.

In the triglyceride determination using the present reagent prepared by using the LPL of the present invention, the time required for absorbance to reach a constant level was about 8 minutes, whereas it was 23 minutes using a reagent prepared by using the LPL of Pseudomonas origin (produced by TOYOBO Ltd.). Thus, the use of the LPL according to the present invention greatly reduces the time required for the determination of triglycerides.

Further, each of a reagent comprising the above-described glycerol color forming solution and 5 μl of the LPL obtained in Example 1 (8 U/ml) and a conventional reagent comprising the same glycerol color forming solution and 5 μl of the LPL of Pseudomonas origin (product of Toyo Spinning Co., Ltd.) (8 U/ml) was allowed to stand at 25° C. for 4 days. Then, the triglyceride content of the above-described control serum preparations was determined with each of the thus preserved reagents. As a result, 100% of the triglycerides were detected using the present reagent in 8 minutes from the start of determination, while only 80% of the triglycerides could be detected using the conventional reagent in 8 minutes.

While the invention has been described in detail and with reference to specific embodiments thereof, it will be apparent to one skilled n the art that various changes and modifications can be made therein without departing from the spirit and scope thereof.

What is claimed is:

1. A reagent comprising a color former and a thermostable lipoprotein lipase for the quantitative determination of triglycerides in body fluids,
   wherein said thermostable liproprotein lipase has an activity to hydrolyze triglycerides in lipoproteins to glycerol and fatty acids, said activity being about 100% retained after treatment in a buffer having a pH of from about 4 to 7 at about 60° C. for about 15 minutes; has a pH optimum of from about 8 to 9; has a temperature optimum of about 50° C.; and
   wherein said thermostable lipoprotein lipase has a glycerol forming activity and a fatty acid forming activity, such that said glycerol forming activity is at least about 15% of said fatty acid forming activity.

2. The reagent according to claim 1, wherein said thermostable lipoprotein lipase is obtained from Streptomyces 7825 (FERM P-9983, FERM BP-2489).

3. The reagent according to claim 1, wherein said thermostable lipoprotein lipase has a molecular weight of about 30–50,000 daltons by gel filtration, and is inhibited by magnesium.

* * * * *